United States Patent
Benndorf et al.

(10) Patent No.: US 7,643,612 B2
(45) Date of Patent: Jan. 5, 2010

(54) DIGITAL X-RAY IMAGING SYSTEM AND METHOD FOR GENERATING AN IMAGE DATASET FOR REPRODUCIBILY GENERATING X-RAY IMAGES

(75) Inventors: Steffen Benndorf, Röthenbach (DE); Michael Fuhrmann, Herzogenaurach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/157,355

(22) Filed: Jun. 10, 2008

(65) Prior Publication Data

US 2008/0310592 A1     Dec. 18, 2008

(30) Foreign Application Priority Data

Jun. 12, 2007    (DE) .................. 10 2007 026 909

(51) Int. Cl.
*H05G 1/64*    (2006.01)
(52) U.S. Cl. .......................... 378/98; 378/62; 378/207
(58) Field of Classification Search ............. 378/62, 378/91, 98, 98.2, 98.7, 116, 207; 250/370.01, 250/370.08, 370.09
See application file for complete search history.

(56) References Cited

U.S. PATENT DOCUMENTS

| 4,209,827 | A | * | 6/1980 | Duinker ....................... 378/21 |
| 5,646,417 | A | | 7/1997 | Deqaele et al. ............. 250/584 |
| 5,757,021 | A | | 5/1998 | Dewaele ..................... 250/581 |
| 6,851,851 | B2 | | 2/2005 | Smith et al. ................. 378/189 |

FOREIGN PATENT DOCUMENTS

| DE | 69409095 T2 | 11/1995 |
| DE | 69530752 T2 | 3/2004 |

OTHER PUBLICATIONS

Alinejat Bengi; Phoenix begeistert die Magnetom World; icare, Siemens Medical Solutions, vol. Jan. 2003, p. 40; Magazine; 2003; DE.

* cited by examiner

*Primary Examiner*—Courtney Thomas

(57) ABSTRACT

Setting information relating to mechanical settings of a digital x-ray imaging system, settings of a control variable or settings of an image processing system, as had been performed during the recording of the relevant digital x-ray image, are stored for a digital x-ray image. It is thereby made possible for an operator to read out the setting information and restore the x-ray image recording situation. The setting conditions can even be restored automatically. This also applies to at least the major part of the mechanical settings.

15 Claims, 1 Drawing Sheet

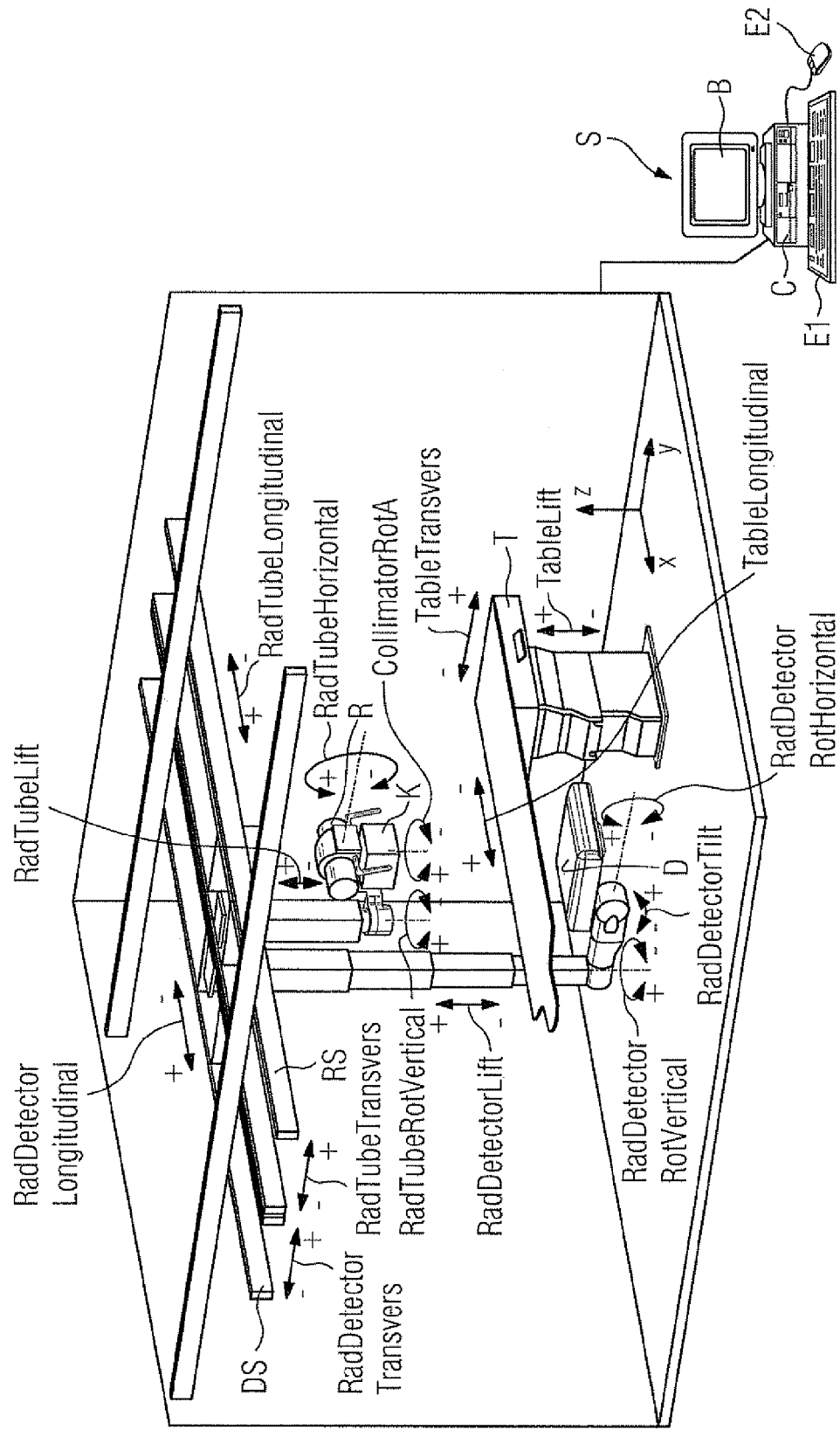

DIGITAL X-RAY IMAGING SYSTEM AND METHOD FOR GENERATING AN IMAGE DATASET FOR REPRODUCIBLY GENERATING X-RAY IMAGES

CROSS REFERENCE TO RELATED APPLICATIONS

This application claims priority of German application No. 10 2007 026 909.0 filed Jun. 12, 2007, which is incorporated by reference herein in its entirety.

FIELD OF THE INVENTION

The invention relates to a digital x-ray imaging system and a method for generating an image dataset by a digital x-ray imaging system. Said method can be used in the case of a method for generating digital x-ray images under reproducible conditions, and the result of the method is an image dataset which is stored on a storage medium for digital data.

BACKGROUND OF THE INVENTION

A plurality of settings are possible in digital x-ray imaging systems. On the one hand these are mechanical settings which are typically carried out prior to an image being recorded. Components which are adjusted mechanically include in particular the radiographic x-ray tube, the digital x-ray detector and usually also the patient examination table on which lies the patient of whom an x-ray image is to be taken. The mechanical settings can also include the setting of a filter if the latter is adjusted by hand by e.g. an operator.

Other settings relate to at least one control variable for the actual x-ray image. An example of a control variable of said kind is the voltage at the voltage generator, which voltage is used for the radiographic x-ray tube. Another control variable, typically specified with the aid of electrical signals, is the exposure time. The filter setting can also be included as a control variable, e.g. if it is electrically controlled and in particular is not associated in any way with mechanically movable components. A control variable can also be a value by means of which the recording system is specified, a distinction being made e.g. between automatic exposure system and two-point technique. The recording system indirectly specifies exposure time and possibly filter setting.

Once the settings have been performed mechanically on the respective components and also those of the control variables, means for capturing digital image information in the digital x-ray imaging system serve to record the actual digital x-ray image, which initially is unprocessed. The digital x-ray image can be stored, where necessary after a processing step, as part of an image dataset in a memory of the digital x-ray imaging system.

Frequently, digital x-ray images, once recorded, are used repeatedly, in particular when the treating physician wishes to observe the course of a medical condition. Typically, the physician will record, or arrange to have recorded, new digital x-ray images each time at various stages of the medical condition. In order to be able to recognize the course of the medical condition particularly well on the basis of the digital x-ray images it is important and advantageous if the later images are recorded using the same settings as the earlier images. In the prior art the persons recording the images attempt to deduce the settings for the image recording situation with the aid of the existing image, and then to reproduce said settings. This is difficult in particular in such cases in which the imaging is not performed fully automatically, but in which the user has to exert an influence over the mechanical settings from the outset, e.g. by hand. For example, certain x-ray images require an oblique irradiation from the tube onto the detector. Positioning, rotating and tilting the x-ray tube are then included among the tasks performed by the user. The lens aperture must also be set by the user. Even if the user subsequently still knows the settings for the voltage generator, he/she receives no help with regard to the alignment of the radiographic x-ray tube and the aperture setting when he/she wishes to restore the image recording situation of an earlier image.

SUMMARY OF THE INVENTION

The object of the invention is to make it easier to reproduce image recording situations.

The object is achieved by the claims.

The digital x-ray imaging system according to the invention comprises means which store setting information relating to the mechanical setting of the at least one component and/or to the setting of the at least one control variable together with the image information, i.e. the actual digital x-ray image, in a respective image dataset. In addition it is aimed to provide means which can read out the setting information when an image dataset is called from the memory.

In a certain way the invention creates a completely new type of image dataset, which is to say that by comparison with prior art image dataset formats the quantity of information contained therein as a result of the setting information is expanded. For example, the setting information can be stored in what is referred to as the DICOM header of a conventional image dataset.

Storing the setting information together with the image information causes an indissoluble connection to be created, and the user is not reliant on laboratory logbooks, etc.

This can already make the user's work easier if he/she typically has to make the mechanical settings by hand. The information relates to the mechanical settings and can then be inputtable by a user. Sensors can also be provided on the respective mechanically settable components, which sensors capture the information relating to the mechanical settings. The setting information thus stored must then, after being read out when the image dataset is called, simply be communicated to an operator, e.g. visually, by being displayed on a monitor screen, if the information is not to be communicated audibly or even haptically.

There are also x-ray imaging systems, and in fact to an increasing extent, in which the mechanical settings are effected by means of servo motors. The setting information relating to the mechanical settings can then simply contain control information for the servo motors. This information can then be used such that means are provided which, after this setting information has been read out, supply control commands to the servo motors based on the control information. In this case the mechanical settings are reproduced automatically and in this regard the user is relieved of his/her activity.

The setting information relating to the setting of at least one control variable can also be used automatically in that after the information is read out suitable setting means are provided for setting the control variable for a subsequent recording of an x-ray image.

A further setting possibility previously not mentioned relates to the image processing. Typically, prior to being stored, the digital image information is subjected to image processing by processing means. A typical image processing operation includes enhancing the contrast of the entire image or increasing the edge contrast.

There can be different settings for the image processing. The digital x-ray imaging system can now also be configured such that the means for storing the setting information also provide the information relating to the settings used for the image processing, which can likewise be read out subsequently, as the setting information stored together with the image information in the respective image dataset. When the information is subsequently read out, it can be provided that after the reading-out, setting means use the setting information for the image processing for adjusting the setting for the image processing of subsequently recorded x-ray images.

The invention also includes a method for generating a subsequently usable image dataset by means of a digital x-ray imaging system, comprising the steps:
a) Performing mechanical settings on the x-ray imaging system,
b) Deriving digital data including information relating to the mechanical settings,
c) Specifying control variables transmitted via electrical signals to parts of the x-ray imaging system (e.g. to the x-ray generator),
d) Deriving digital data including information relating to the control variables,
e) Recording a digital x-ray image,
f) Processing the digital x-ray image by means of an image processing system in accordance with selectable settings,
g) Deriving digital data including information relating to the settings used in step f),
h) Storing the processed digital x-ray image in an image dataset together with the digital data derived in step b) and/or in step d) and/or in step f).

According to the problem presented in the introduction, an image dataset generated by the method can be used for the reproducible generation of digital x-ray images.

Thus, the invention also includes a method for the reproducible generation of digital x-ray images. A prerequisite is that the information derived in step b) of the method is contained in the image dataset. Then follow the additional steps:
i) Reading out the information derived in step b) from the image dataset,
k) Performing the mechanical settings on the x-ray imaging system on the basis of the information read out in step i),
n) Recording a further digital x-ray image.

In the case of the additional digital x-ray image thus recorded, the mechanical settings are identical to the mechanical settings that were performed for the previously recorded x-ray image. As a result, already because of the same image perspective, there is a similarity between the digital x-ray images recorded in step e) on the one hand and the digital x-ray images recorded in step n) on the other.

Step k) is preferably performed automatically in this case too, and moreover on the basis of the information read out in step i) control commands for motors are derived or sent to the latter, and the mechanical settings are then effected by said motors.

Naturally the digital data derived in step d) and the digital data derived in step g) can also be used if said data was stored in the image dataset in step a).

In the former case the method for reproducible generation of images can additionally comprise the following steps:
l) Reading out the digital data derived in step d) from the image dataset,
m) Specifying the control variable on the basis of the digital data read out in step l).

In the second case the method can include the following steps:
o) Reading out the digital data derived in step g) from the image dataset,
p) Processing the digital x-ray image recorded in step n) by means of the image processing system on the basis of settings based on the digital data read out in step o).

In one case, therefore, the control variables are the same for the recording of both x-ray images. In the other case, both x-ray images are processed in the same way.

The invention also includes the provisioning of the respective image dataset as such. Therefore it also relates to a storage medium for digital data, on which storage medium at least one image dataset is stored. The stored image dataset therefore comprises a first data part containing grayscale values of a digital x-ray image and a second data part containing information relating to settings of an x-ray imaging system that were used for the recording and/or processing of the digital x-ray image.

The advantage of providing x-ray images of said kind has already been explained above: Additional digital x-ray images can be generated, and moreover under conditions that are reproduced with respect to the original conditions.

BRIEF DESCRIPTION OF THE DRAWINGS

A preferred embodiment of the invention is described below with reference to the drawing, wherein the FIGURE illustrates a digital x-ray imaging system which can be used in an optimal manner in connection with the present invention.

DETAILED DESCRIPTION OF THE INVENTION

The digital x-ray imaging system depicted in the FIGURE is in the present case shown in an outlined room from the ceiling of which two supports hang down, namely a first support RS for the radiographic x-ray tube R and a second support DS for the one digital x-ray detector D. Also contained in the room is a patient examination table T.

The supports DS and RS can travel as a whole across the ceiling, more specifically in the y-direction according to the coordinate system shown. In the drawing the associated parameters are called RadDetectorTransvers and RadTubeTransvers. The supports can also travel in the x direction; see parameters RadDetectorLongitudinal and RadTubeLongitudinal. The radiographic x-ray tube R and detector D can also each be moved in the z-direction; see parameters RadDetectorLift and RadTubeLift. The radiographic x-ray tube R and detector D can be rotated vertically; see parameters RadDetectorRotVertical and RadTubeRotVertical, and they are also rotatable horizontally in an axis normal hereto; see parameters RadDetectorRotHorizontal and RadTubeHorizontal. The detector D is also tiltable; see parameter RadDetectorTilt. On the radiographic x-ray tube R, the collimator K can be rotated; see parameter CollimatorRotA.

The table T is movable in all three coordinate directions; see parameters TableLongitudinal, TableTransvers and TableLift.

It is provided that almost all the movement options are effected with the aid of motors (not shown in the FIGURE). An exception can be provided only for the movement of the table T in the x-y plane, i.e. the parameters TableLongitudinal and TableTransvers must then be set manually by an operator.

The digital x-ray imaging system includes a control unit S with central computer C to which a monitor B is connected and to which input units E1 (keyboard) and E2 (computer mouse) are assigned. The motors can be controlled by way of the input units for the purpose of setting the above-mentioned parameters. In the case of the central control unit S it can also be provided that joysticks (not shown) are made available for individual parameters.

The operator recording the x-ray images will now set all the parameters very carefully for a first recording, e.g. by way of the input units E1 and E2. The actuating commands to the respective motors or at least the information corresponding to the respective end position are stored. The table is moved by hand if necessary, and the parameters TableLongitudinal and TableTransvers are input via the input unit E1 and likewise stored. The operator now records at least one digital x-ray image. All the information needed in order to be able to perform the same mechanical settings subsequently is stored for said digital x-ray image in its DICOM header. Basically, information must be stored for each of the cited parameters.

The user can upload the digital x-ray image at a later time after a certain period of time has elapsed and the x-ray imaging system has possibly been used for some other purpose. In this way the additional information (setting information) also stored for the digital x-ray image will be read out. Preferably the motors are now controlled automatically in such a way that the status that obtained when the uploaded x-ray image was recorded is restored. If the parameters relate to TableLongitudinal and TableTransvers, the respective information must be displayed to the operator e.g. on the monitor screen B so that these settings can be re-established manually.

Further information relating to other settings can also be stored in addition to the information relating to the mechanical settings. An example of other settings requiring to be directly assigned to the x-ray image are the voltage generated by the voltage generator (not shown in the FIGURE) for the radiographic x-ray tube R, the exposure time and where applicable the type of filtering. Settings used for possible image processing of the digital x-ray image prior to its being stored, e.g. settings by means of which the contrast enhancement, e.g. of the entire image or of individual edges, in the x-ray image is defined, can also be stored as additional information.

If corresponding data is contained in the DICOM header of the x-ray images, it can likewise be read out again when the x-ray images are called and the same settings can be restored automatically, i.e. the control system S can output electrical signals by means of which the settings of certain variables can be re-established, and the settings that were used for the original, now uploaded x-ray image can likewise be provided again automatically in the image processing system.

The invention claimed is:

1. A digital x-ray imaging system for generating a digital image at a mechanical setting and a control variable setting of the digital x-ray imaging system, comprising:
    a component that captures the digital image at the mechanical setting and the control variable setting; and
    a control unit that:
      derives a digital data of the mechanical setting;
      specifies a control variable of the digital x-ray imaging system for the control variable setting;
      derives a digital data of the control variable setting;
      processes the digital x-ray image based on an image processing setting;
      deriving a digital data of the image processing setting;
      stores the processed digital x-ray image together with the digital data of the mechanical setting, the control variable setting, and the image processing setting; and
      reads out the digital data of the mechanical setting, the control variable setting, and the image processing setting.

2. The digital x-ray imaging system as claimed in claim 1, wherein the component of the digital x-ray imaging system comprises an x-ray tube, an x-ray detector, and a patient table.

3. The digital x-ray imaging system as claimed in claim 1, wherein the digital data of the mechanical setting is input by an operator or captured by a sensor.

4. The digital x-ray imaging system as claimed in claim 3, wherein the digital data of the mechanical setting is communicated to the operator after the digital data of the mechanical setting is read out.

5. The digital x-ray imaging system as claimed in claim 1, wherein the mechanical setting is controlled by a servo motor and the digital data of the mechanical setting comprises control information of the servo motor.

6. The digital x-ray imaging system as claimed in claim 5, wherein the servo motor is subsequently controlled based on the control information of the servo motor after the digital data of the mechanical setting is read out.

7. The digital x-ray imaging system as claimed in claim 1, wherein a subsequent digital image is reproducibly captured by the digital x-ray imaging system at the mechanical setting after the digital data of the mechanical setting is read out.

8. The digital x-ray imaging system as claimed in claim 1, wherein a subsequent digital image is reproducibly captured by the digital x-ray imaging system at the control variable setting after the digital data of the control variable setting is read out.

9. The digital x-ray imaging system as claimed in claim 1, wherein a subsequent digital image captured by the digital x-ray imaging system is processed based on the digital data of the image processing setting.

10. A method for generating a digital x-ray image by a digital x-ray imaging system, comprising:
    setting a component of the digital x-ray imaging system for a mechanical setting;
    deriving a digital data of the mechanical setting;
    specifying a control variable of the digital x-ray imaging system for a control variable setting;
    deriving a digital data of the control variable setting;
    capturing a digital x-ray image at the mechanical setting and the control variable setting;
    processing the digital x-ray image based on an image processing setting;
    deriving a digital data of the image processing setting; and
    storing the processed digital x-ray image together with the digital data of the mechanical setting, the control variable setting, and the image processing setting.

11. The method as claimed in claim 10, wherein the mechanical setting is controlled by a servo motor and the digital data of the mechanical setting comprises control information of the servo motor.

12. The method as claimed in claim 11, further comprising:
    reading out the digital data of the mechanical setting, and
    subsequently controlling the servo motor based on the control information of the servo motor after the reading out.

13. The method as claimed in claim 10, further comprising:
    reading out the digital data of the mechanical setting, and
    reproducibly capturing a further digital x-ray image by the digital x-ray imaging system at the mechanical setting after the reading out.

14. The method as claimed in claim 10, further comprising:
    reading out the digital data of the control variable setting, and
    reproducibly capturing a further digital x-ray image by the digital x-ray imaging system at the control variable setting after the reading out.

15. The method as claimed in claim 10, further comprising:
    reading out the digital data of the image processing setting, and
    subsequently processing a further digital x-ray image captured by the digital x-ray imaging system based on the digital data of the image processing setting after the reading out.

* * * * *